US012723274B2

(12) United States Patent
Ping et al.

(10) Patent No.: US 12,723,274 B2
(45) Date of Patent: Sep. 1, 2026

(54) METHOD AND DEVICE FOR FIXED-POINT EDITING OF NUCLEOTIDE SEQUENCE WITH STORED DATA

(71) Applicant: BGI SHENZHEN, Shenzhen (CN)

(72) Inventors: Zhi Ping, Shenzhen (CN); Xiaoluo Huang, Shenzhen (CN); Shihong Chen, Shenzhen (CN); Chen Chai, Shenzhen (CN); Yue Shen, Shenzhen (CN); Xun Xu, Shenzhen (CN); Huanming Yang, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 1380 days.

(21) Appl. No.: 17/417,702

(22) PCT Filed: Dec. 26, 2018

(86) PCT No.: PCT/CN2018/123858

§ 371 (c)(1),
(2) Date: Jun. 23, 2021

(87) PCT Pub. No.: WO2020/132935

PCT Pub. Date: Jul. 2, 2020

(65) Prior Publication Data

US 2022/0064705 A1 Mar. 3, 2022

(51) Int. Cl.

| | |
|---|---|
| ***G01N 33/48*** | (2006.01) |
| ***C12Q 1/6806*** | (2018.01) |
| ***G11C 13/00*** | (2006.01) |

(52) U.S. Cl.

CPC ........ *C12Q 1/6806* (2013.01); *G11C 13/0019* (2013.01)

(58) Field of Classification Search

None

See application file for complete search history.

(56) References Cited

U.S. PATENT DOCUMENTS

2019/0355442 A1* 11/2019 Merriman .......... G01N 27/4145

FOREIGN PATENT DOCUMENTS

| | | | |
|---|---|---|---|
| CN | 104850760 | A | 8/2015 |
| CN | 106845158 | * | 6/2017 |
| CN | 106845158 | A | 6/2017 |
| CN | 108875312 | A | 11/2018 |
| WO | WO 2013/178801 | A2 | 12/2013 |
| WO | WO 2013/178801 | A3 | 12/2013 |
| WO | WO 2014/014991 | A2 | 1/2014 |
| WO | WO 2014/014991 | A3 | 1/2014 |
| WO | WO 2017/083177 | A1 | 5/2017 |
| WO | WO 2018/081566 | A1 | 5/2018 |
| WO | WO 2018/094115 | A1 | 5/2018 |
| WO | WO 2018/132457 | A1 | 7/2018 |
| WO | WO 2018/148257 | A1 | 8/2018 |
| WO | WO 2018/148260 | A1 | 8/2018 |
| WO | WO 2018/156792 | A1 | 8/2018 |

OTHER PUBLICATIONS

Ludwig, Wolfgang, et al. "ARB: a software environment for sequence data." Nucleic acids research 32.4 (2004): 1363-1371.*

* cited by examiner

*Primary Examiner* — Anna Skibinsky

(74) *Attorney, Agent, or Firm* — James S. Keddie; Bozicevic, Field & Francis LLP

(57) ABSTRACT

Disclosed are a method and device for fixed-point editing of a nucleotide sequence stored with data.

9 Claims, 2 Drawing Sheets

Specification includes a Sequence Listing.

METHOD AND DEVICE FOR FIXED-POINT EDITING OF NUCLEOTIDE SEQUENCE WITH STORED DATA

CROSS-REFERENCE TO RELATED APPLICATIONS

This application is a § 371 national phase of International Application No. PCT/CN2018/123858, filed on Dec. 26, 2018, which application is incorporated by reference herein.

TECHNICAL FIELD

The present disclosure pertains to the field of molecular biology, in particular to the technical field of nucleic acid storage, and more specifically relates to a method and a corresponding device for fixed-point editing of a nucleic acid sequence with stored data.

BACKGROUND ART

With the development of modern technology, especially Internet and big data, global data is showing an exponential increase. The ever-increasing amount of data places higher and higher requirements on storage technology. Traditional storage technologies, such as magnetic tape and optical disc storage, are increasingly unable to meet current data requirements due to limited storage density and time.

The DNA storage technology developed in recent years provides a new way to solve these problems. DNA (deoxyribonucleotide) is a double strand structure composed of deoxyribose and four nitrogen-containing bases (adenine (A), thymine (T), cytosine (C), guanine (G)), is the carrier of genetic information, which controls the development and continuation of life and the operation of life functions. DNA is one of the most dense and stable information storage carriers known in the nature. The development of DNA synthesis and sequencing technology makes it possible to become a digital information storage carrier. Compared with traditional storage media, DNA as a medium for information storage has characteristics such as a long storage time (up to thousands of years, which is more than a hundred times that of existing magnetic tape and optical disk media), a high storage density (up to $10^9$ Gb/mm$^3$, which is more than ten million times that of magnetic tape and optical disk media), and good storage security.

DNA data storage usually comprises the following steps: 1) Encoding: converting a binary 0/1 code of computer information into A/T/C/G DNA sequence information; 2) Synthesis: synthesizing DNA molecules with corresponding sequences by DNA synthesis technology, and storing the obtained synthetic DNA molecules in in vitro media or living cells; 3) Sequencing: reading the DNA sequence of the stored DNA molecules by sequencing technology; 4) Decoding: converting the DNA sequence obtained by sequencing into the binary 0/1 code by the method corresponding to the encoding process in step 1), and further converting it into computer information. In order to achieve effective DNA data storage, it is necessary to further develop technology for the above steps.

CONTENTS OF THE INVENTION

The inventors of the present disclosure have discovered that the existing DNA storage methods have the problems that fixed-point modification, addition and deletion are impossible. The existing DNA storage methods are all for the purpose of one-time synthesis to store data and information for long-term preservation. Assuming that after the synthesis is completed, it is found that the original information to be stored is wrong, or when an individual error occurs during synthesis and cannot be recovered by encoding an error correction code, the existing methods can only discard all the originally synthesized DNA and re-synthesize it, thereby greatly reducing the fault tolerance rate of DNA storage. In response to the above-mentioned problems, the present disclosure proposes a method for fixed-point editing of a nucleic acid sequence with stored data and a corresponding device.

In the first aspect, the present disclosure provides a method for fixed-point editing of a nucleic acid sequence with stored data, which comprises the following steps:

(1) splitting a nucleic acid sequence in which a data is stored into a plurality of sequence fragments, and dividing all the sequence fragments into i partitions, wherein i is a positive integer;

(2) adding a partition adapter at one or both ends of the sequence fragments in each partition, wherein the partition adapter sequence for each partition is different from each other;

(3) synthesizing the sequence fragments in each partition as described in the synthesis step (2) to obtain nucleic acid fragments;

(4) determine a partition n where a sequence fragment to be edited is located, and record it as the $n^{th}$ partition;

(5) amplifying the sequence fragments of all partitions except for the sequence fragments of the $n^{th}$ partition by using a partition primer library, wherein the partition primer library comprises primers that are at least partially complementary to the partition adapter sequences of the $1^{st}$ partition, the $2^{nd}$ partition, . . . , the $n-1^{th}$ partition, the $n+1^{th}$ partition, . . . , and the $i^{th}$ partition, respectively, so as to obtain a library comprising the sequence fragments of the $1^{st}$ partition, the $2^{nd}$ partition, . . . , the $n-1^{th}$ partition, the $n+1^{th}$ partition, . . . , and the $i^{th}$ partition; and (6) correcting a wrong sequence in the sequence fragment to be edited in the $n^{th}$ partition to obtain a correct sequence, then synthesizing all sequence fragments in the $n^{th}$ partition according to the correct sequence, and adding them into the library of step (5) so as to obtain a library with the correct sequence.

In a specific embodiment, in step (1), the data is text information, image information, or sound information.

In a specific embodiment, before step (1), the data is encoded into binary data according to a first encoding rule. The first encoding rule is a binary encoding rule known to those skilled in the art.

In a specific embodiment, before step (1), the binary data is encoded into a nucleic acid sequence through a second encoding rule, so as to obtain the nucleic acid sequence in which the data is stored. The second encoding rule is known to those skilled in the art, in which the second encoding rule includes but is not limited to Huffman Encoding Rule, Fountain Code Encoding Rule, XOR Encoding Rule, Grass Encoding Rule.

In a specific embodiment, in step (1), the nucleic acid sequence in which a data stored is split into a plurality of sequence fragments. The length of the sequence fragments is not particularly limited, but taking into account the convenience of synthesis in step (3) and the limitations of synthesis technology, the nucleic acid sequence in which a data is stored can generally be split into sequence fragments of not exceeding 200 nt. The length of each fragment may be the same or different, and preferably the nucleic acid sequence is split into sequence fragments of the same length.

In a specific embodiment, in step (1), all sequence fragments are divided into i partitions, wherein i is a positive integer. The number of sequence fragments contained in each partition can be the same or different.

In a specific embodiment, in step (2), a partition adapter A1 is added at one or both ends of each sequence fragment in the $1^{st}$ partition, a partition adapter A2 is added at one or both ends of each sequence fragment in the $2^{nd}$ partition, . . . , a partition adapter Ai is added at one or both ends of all sequence fragments in the $i^{th}$ partition, wherein the partition adapter sequences are different from each other but have the same length, which is preferably 16-20 nt.

In another specific embodiment, in step (2), at the 5'end of the sequence fragment of each partition, a forward partition adapter of the partition is added, and at the 3'end of the sequence fragment of each partition, a reverse partition adapter of the partition is added. Specifically, in step (2), a partition adapter A1 is added at the 5'end of each sequence fragment in the $1^{st}$ partition, and a partition adapter A1' is added at the 3'end of each sequence fragment in the $1^{st}$ partition, a partition adapter A2 is added at the 5'end of each sequence fragment in the $2^{nd}$ partition, a partition adapter A2' is added at the 3'end of each sequence fragment in the $2^{nd}$ partition, . . . , a partition adapter Ai is added at the 5'end of each sequence fragment in the $i^{th}$ partition, and a partition adapter Ai' is added at the 3'end of each sequence fragment in the $i^{th}$ partition, wherein the partition adapter sequences are different from each other but have the same length, which is preferably 16-20 nt.

In another specific embodiment, in step (2), a universal adapter is added at the 5'end of the sequence fragments of each partition, and a partition adapter of the partition is added at the 3'end of the sequence fragment of each partition. Specifically, in step (2), a universal adapter A is added at the 5'end of the sequence fragments of each partition, a partition adapter A1 is added at the 3'end of each sequence fragment in the $1^{st}$ partition, a partition adapter A2 is added at the 3'end of each sequence fragment in the $2^{nd}$ partition, . . . , a partition adapter Ai is added at the 3'end of each sequence fragment in the $i^{th}$ partition, so as to result in: in the $1^{st}$ partition the 5'end of each sequence fragment is connected with the universal adapter A and the 3'end is connected with the partition adapter A1, in the $2^{nd}$ partition the 5'end of each sequence fragment is connected with the universal adapter A and the 3'end is connected with the partition adapter A2, . . . , in the $i^{th}$ partition the 5'end of each sequence fragment is connected with the universal adapter A and the 3'end is connected with the partition adapter Ai; wherein the partition adapter sequences are different from each other but have the same length, which is preferably 16-20 nt.

In another specific embodiment, in step (2), a universal adapter A is added at the 3'end of the sequence fragments in each partition, a partition adapter A1 is added at the 5'end of each sequence fragment in the $1^{st}$ partition, a partition adapter A2 is added at the 5'end of each sequence fragment in the $2^{nd}$ partition, . . . , a partition adapter Ai is added at the 5'end of each sequence fragment in the $i^{th}$ partition, wherein the partition adapter sequences are different from each other but have the same length, which is preferably 16-20 nt.

In the present disclosure, the partition adapter is designed according to the following rules including but not limited to: 1) the occurrence of consecutive 4 or more single bases shall be avoided, that is, "AAA" is acceptable but "AAAA" is not acceptable; 2) the tandem repeats or complementary repeats of 3 or more bases shall not occur, that is, tandem repeats such as "ATCATCATC" and complementary repeats such as "ATCXXXGAT" are not acceptable; 3) the DNA or RNA secondary structure shall not occur; 4) different adapters shall not form a dimer; 5) adapter sequences and the sequence fragment to be stored shall have as little overlap ratio as possible.

In a specific embodiment, the partition adapters can be arranged in binary size (i.e., A or T represents 0, C or G represents 1; or A or C represents 0, T or G represents 1, etc., there are a total of 12 combinations), or arranged in quaternary size (for example: A="0", T="1", C="2", G="3", there are a total of 24 ways), so as to achieve the purpose of adding index numbers, and based on the index numbers, the partition sequences can be assembled according to the number sequence.

In another specific embodiment, the method further comprises: adding an index number to each sequence fragment after obtaining the sequence fragments to which the partition adapter is added in step (2), wherein the index number is adjacent to the partition adapter. Specifically, the index number is an index code formulated in accordance with the rules, such as "AAAA"=1, "CCCC"=2, "TTTT"=3, "GGGG"=4, "ATCG"=5, etc. Those skilled in the art can understand that the rules are user-defined rules, and as long as the rules can realize one-to-one correspondence between the index code and the position sequence information of the sequence, the specific encoding rules are not limited. Furthermore, those skilled in the art can understand that an index number is added to each sequence fragment, as long as the index number is adjacent to the partition adapter, the specific position where the index number is added is not limited. For example, after adding an index number to the 5'end of a sequence fragment, the followings are formed from the 5' to the 3'end of the sequence: "partition adapter-index number-sequence fragment with data stored-partition adapter", "universal adapter-index number-sequence fragment with data stored-partition adapter" or "partition adapter-index number-sequence fragment with data stored-universal adapter"; for another example, after adding an index number to the 3'end of a sequence fragment, the followings are formed from 5' to 3'end of the sequence: "partition adapter-sequence fragment with data stored-index number-partition adapter", "partition adapter-sequence fragment with data stored-index number-universal adapter" or "universal adapter-sequence fragment with data stored-index number-partition adapter".

In a specific embodiment, the partition adapter has a length of 18 nt, and the index number sequence has a length of 5 nt to 10 nt, preferably 6 nt.

In a specific embodiment, the partition n where the sequence fragment to be edited is located is determined according to the encoding rule used when the data is stored. When the stored data needs to be edited, such as the original data itself has an error that needs to be corrected, the partition n where the error data is located is found according to the encoding rule that is used when the data is stored, such as binary encoding rules, Huffman encoding rules, fountain code encoding rules, XOR encoding rules, or Grass encoding rules, etc.

In another specific embodiment, the partition n where the sequence fragment to be edited is located is determined by sequencing the nucleic acid sequence fragment synthesized in step (3) and performing sequence alignment.

In a specific embodiment, in step (5), a multiplex PCR is used to amplify the sequence fragments. In the present disclosure, the multiplex PCR can be performed by those skilled in the art according to the prior art knowledge. The multiplex PCR process can include but not be limited to Touch up, Touch down and other forms of PCR. The polymerases used can include but not be limited to Taq, Phusion, Q5, Vent, KlenTaq and other different types of enzymes or their combinations in different proportions.

Those skilled in the art can understand that the primer sequences in the partition primer library described in step (5) are at least partially complementary to the partition adapter sequence described in the first aspect of the present disclosure, and the partition primer library comprises primers that are at least partially complementary to the partition adapter sequences of the $1^{st}$ partition, the $2^{nd}$ partition, . . . , the $n-1^{th}$ partition, the $n+1^{th}$ partition, . . . , and the $i^{th}$ partition, respectively.

After the amplification in step (5), the sequence fragments of all partitions except for the sequence fragments of the $n^{th}$ partition are amplified, so as to obtain a library comprising the sequence fragments of the $1^{st}$ partition, the $2^{nd}$ partition, . . . , the $n-1^{th}$ partition, the $n+1^{th}$ partition, . . . , and the $i^{th}$ partition. The sequences in the $n^{th}$ partition has not undergone exponential amplification, so its copy number is much smaller than the correct sequences of other partitions that have undergone exponential amplification.

Those skilled in the art can understand that through multiplex PCR amplification, the purpose of diluting the sequence fragments of the $n^{th}$ partition can be achieved. In this application, the dilution refers to increasing the copy number of the target fragments through exponential amplification, so that the proportion of non-target fragments that have not been exponentially amplified is significantly reduced in the final product, thereby achieving the purpose of dilution. For example, exponential amplification of all sequence fragments other than the $n^{th}$ partition is performed for 30 cycles. Theoretically, the sequences are amplified by $10^9$ times, and the sequence fragments in the $n^{th}$ partition will undergo only linear amplification due to the existence of universal adapter, that is, they will be theoretically amplified by 32768 times ($10^5$). Therefore, in the final amplified product, the proportion of sequence fragments in the $n^{th}$ partition is significantly reduced.

Next, according to the corresponding encoding rules, the wrong sequence in the sequence fragment to be edited in the $n^{th}$ partition can be re-encoded to obtain the correct sequence, and all sequence fragments in the $n^{th}$ partition can be synthesized according to the correct sequence, and then it is mixed with the library comprising the sequence fragments of the $1^{st}$ partition, the $2^{nd}$ partition, . . . , the $n-1^{th}$ partition, the $n+1^{th}$ partition, . . . , and the $i^{th}$ partition, so as to obtain a library with the correct sequence.

Optionally, the sequence fragments in the library can be ligated into a vector, or the sequence fragments in the library can be assembled.

Optionally, the library with the correct sequence, the vector ligated with the sequence fragments, or the assembled sequence fragments can be stored in a medium, wherein the medium includes but is not limited to liquid phase, dry powder, living cells and the like.

In the method of the present disclosure, a "index-partition" method is used to locate the nucleic acid sequence that needs to be edited, and the erroneous data that occurs during the storage process can be corrected at a low cost. Compared with the existing DNA storage methods, this method greatly reduces the correction cost when errors occur in the stored information, and at the same time, greatly improves the fault tolerance rate of the existing DNA storage systems.

In a second aspect, the present disclosure provides a decoding method, comprising sequencing the library obtained by using the method described in the first aspect of the present disclosure to obtain each sequence fragment; and obtaining the position sequence information of each sequence fragment according to the index number of the each sequence fragment; splicing the sequence fragments according to the position sequence information into a nucleic acid sequence in which the data is stored.

Optionally, the obtained nucleic acid sequence in which the data is stored is transcoded into a corresponding binary code, and then the binary code is transcoded into a corresponding data information.

In a specific embodiment, the obtained nucleic acid sequence in which the data is stored is transcoded into the corresponding binary code through the second encoding rule, and then the binary code is transcoded into the corresponding data information through the first encoding rule, wherein, the first encoding rule and the second encoding rule are as defined in the first aspect of the present disclosure.

In a third aspect, the present disclosure provides a device for fixed-point editing of a nucleic acid sequence in which a data is stored, comprising: a module for splitting sequence and dividing partitions, which is configured to split the nucleic acid sequence in which the data is stored into a plurality of sequence fragments, and to divide all the sequence fragments into i partitions, wherein i is a positive integer; a module for adding partition adapter, which is configured to add a partition adapter at one or both ends of the sequence fragments in each partition, wherein the partition adapter sequence of each partition is different from each other; a module for synthesizing nucleic acid, which is configured to synthesize nucleic acid fragments for the sequence fragments with the added partition adapters; a positioning module, which is configured to determine the partition n where a sequence fragment to be edited is located, and record it as the $n^{th}$ partition; an amplification module, which is configured to amplify the sequence fragments of all partitions except for the sequence fragments of the $n^{th}$ partition by using a partition primer library, wherein the partition primer library comprises primers that are at least partially complementary to the partition adapter sequences of the $1^{st}$ partition, the $2^{nd}$ partition, . . . , the $n-1^{th}$ partition, the $n+1^{th}$ partition, . . . , and the $i^{th}$ partition, respectively, so as to obtain a library comprising the sequence fragments of the $1^{st}$ partition, the $2^{nd}$ partition, . . . , the $n-1^{th}$ partition, the $n+1^{th}$ partition, . . . , and the $i^{th}$ partition; and a correction module, which is configured to correct a wrong sequence in a sequence fragment to be edited in the $n^{th}$ partition to obtain a correct sequence, then synthesize all the sequence fragments in the $n^{th}$ partition according to the correct sequence and add them to the library obtained by the amplification module, so as to obtain a library with the correct sequence.

Optionally, the device further comprises a module for adding index number, which is configured to add an index number to the sequence fragment to which a partition adapter is added, wherein the index number is adjacent to the partition adapter.

The length of the sequence fragments and the number of sequence fragments contained in each partition are as defined in the first aspect of the present disclosure.

The partition adapter and the index number are as defined in the first aspect of the present disclosure.

Optionally, the device further comprises an assembly module, which is configured to assemble each sequence fragment in the library.

Optionally, the device further comprises a module for ligating vector, which is configured to ligate each sequence fragment in the library to a vector.

Optionally, the device further comprises a medium storage module, which is configured to store each sequence fragment in the library in a medium, or store the vector ligated with sequence fragment in a medium, or store the assembled sequence fragments in a medium; wherein, the medium includes, but is not limited to, liquid phase, dry powder, living cells, and the like.

In a fourth aspect, the present disclosure provides a decoding device, comprising: a sequencing module, which is configured to sequence a library obtained by using the method described in the first aspect of the present disclosure to obtain each sequence fragment; a module for acquiring position information, which is configured to obtain the position sequence information of the each sequence fragment according to the index number of the each sequence fragment; a splicing module, which is configured to splice the each sequence fragment according to the position sequence information to form a nucleic acid in which the data is stored.

Optionally, the decoding device further comprises a transcoding module, which is configured to transcode the nucleic acid sequence in which the data is stored into a corresponding binary code, and then transcode the binary code into a corresponding data information.

In a specific embodiment, the transcoding module uses a second encoding rule to transcode the obtained nucleic acid sequence in which the data is stored into the corresponding binary code, and then uses a first encoding rule to transcode the binary code into the corresponding data information, wherein the first coding rule and the second coding rule are as defined in the first aspect of the present disclosure.

In a fifth aspect, the present disclosure provides a computer-readable storage medium, on which a computer program is stored, and when the program is executed by a processor, at least one of the following methods is implemented: the method for fixed-point editing of a nucleic acid sequence in which the data is stored according to the first aspect of the present disclosure, and the decoding method as described in the second aspect of the present disclosure.

Through the following detailed description of exemplary examples of the present disclosure with reference to the accompanying drawings, other features and advantages of the present disclosure will become clear.

BRIEF DESCRIPTION OF THE DRAWINGS

The drawings described here are used to provide a further understanding of the present disclosure and constitute a part of the application. The exemplary examples of the present disclosure and the description thereof are used to explain the present disclosure, and do not constitute an improper limitation of the present disclosure. In the attached drawings.

SPECIFIC MODELS FOR CARRYING OUT THE INVENTION

Figure 1:
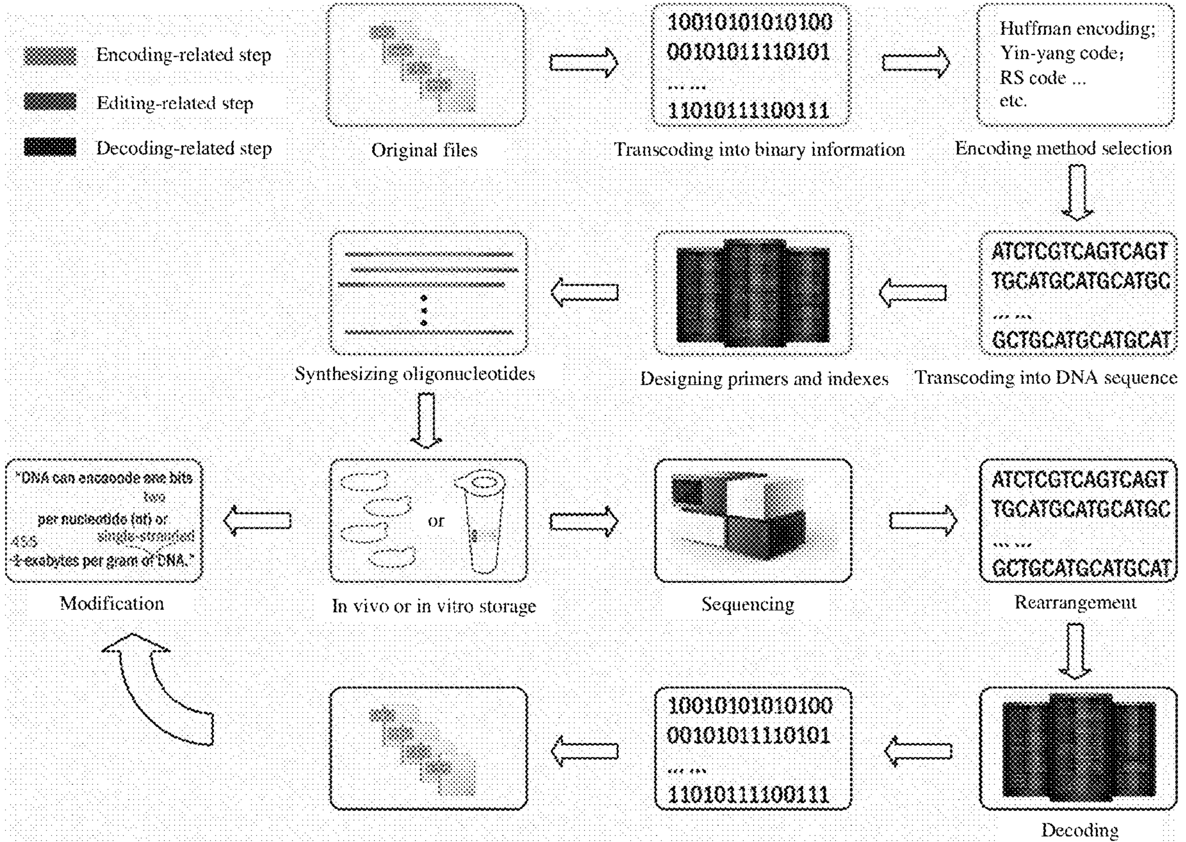
FIG. 1 shows a flowchart of DNA storage.
Figure 2:
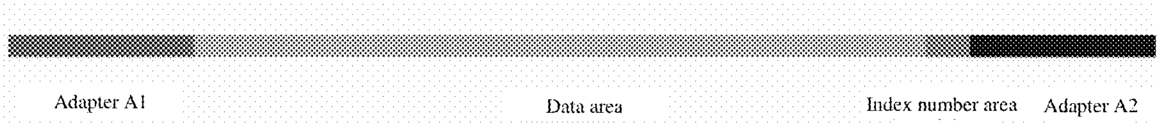
FIG. 2 shows a schematic diagram of sequence fragments after splitting according to some examples of the present disclosure.
Figure 3:
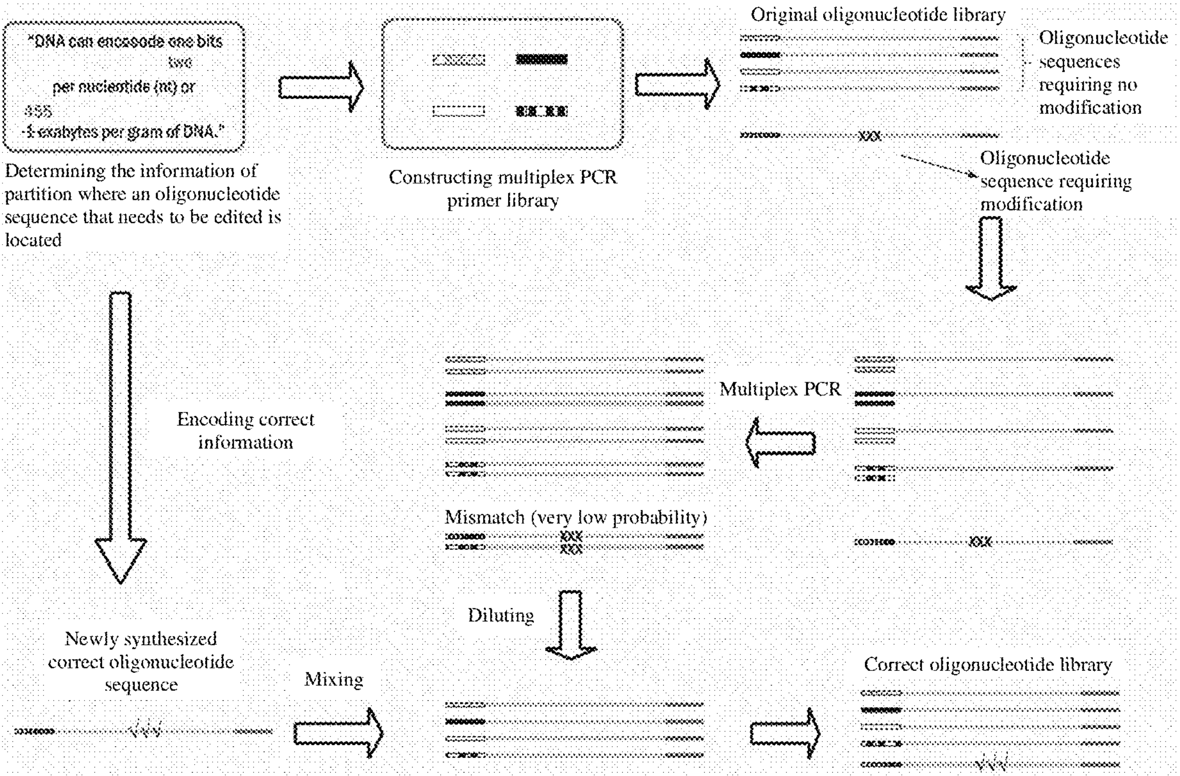
FIG. 3 shows a flowchart of DNA storage sequence fixed-point editing process according to some examples of the present disclosure.

The following will clearly and completely describe the technical solutions in the examples of the present disclosure with reference to the accompanying drawings in the examples of the present disclosure. Obviously, the described examples are only a part of the examples of the present disclosure, rather than all the examples. The following description of at least one exemplary example is actually only illustrative, and in no way serves as any limitation to the present disclosure and its application or use. Based on the examples of the present disclosure, all other examples obtained by those of ordinary skill in the art without creative work shall fall within the protection scope of the present disclosure.

Unless specifically stated otherwise, the relative arrangement of components and steps, numerical expressions and numerical values set forth in these examples do not limit the scope of the present disclosure. At the same time, it should be understood that, for ease of description, the sizes of the various parts shown in the drawings are not drawn in accordance with actual proportional relationships. The technologies, methods and equipment known to those of ordinary skill in the relevant fields may not be discussed in detail, but where appropriate, the technologies, methods and equipment should be regarded as part of the description of the granted patent. In all examples shown and discussed herein, any specific value should be interpreted as merely exemplary, rather than as a limitation. Therefore, other examples of the exemplary examples may have different values. It should be noted that similar reference numerals and letters indicate similar items in the following drawings, so once an item is defined in one drawing, it does not need to be further discussed in the subsequent drawings.

Example 1. Fixed-Point Editing of Nucleic Acid Sequence with Stored Data

Original document: Two sonnets by Shakespeare (English)

Simulation scenario: After the DNA sequences were synthesized, it was found that the stored original file was wrong, and the synthesized sequence needs to be subjected to modification and addition operations.

Experiment Process:

1. The wrong version of the original file was encoded on a computer terminal by Church simple code [Next-Generation Digital Information Storage in DNA George M. Church, Yuan Gao and Sriram Kosuri (Aug. 16, 2012) Science 337 (6102), 1628. [doi: 10.1126/science.1226355]] in combination with Reed Solomon error correction code to obtain 176 sequences, in which "Like feeble old man" in line 11 of the wrong version should be "Like feeble age" in the original text, and "Lord of my" in line 17 of the wrong version should be "Lord of my love" in the original text.
2. After encoding, all sequences were divided into 8 partitions, and 176 DNA sequences with length of 114 were obtained by adding index numbers and partition adapters (in total of 8, A to H) to each sequence and adding universal adapter ATGGTCAGATCGTGCATC, and each partition comprised 22 DNA sequences. Partition A comprised the sequences 1 to 22, in which the 5'end of each sequence was added with the universal adapter, and the 3'end was added with the partition adapter of Partition A; Partition B comprised the sequences 23 to 44, in which the 5'end of each sequence was added with the universal adapter, and the 3'end was added with the partition adapter of Partition B; . . . ; Partition H comprised the sequences 155 to 176, in which the 5'end of each sequence was added with the universal adapter, and the 3'end was added with the partition adapter of Partition H. The sequences of the partition adapters of Partitions A to H were different from each other, and all had a length of 18 nt.

The structure of each sequence from 5' to 3' was: universal adapter-sequence in which information was to be stored-index number-partition adapter.

3. The 176 sequences obtained in step 2 were synthesized.
4. After sequence alignment, it was found that the content to be modified in line 11 was in the 58$^{th}$ sequence in Partition C, and its wrong version sequence was:

```
ATGGTCAGATCGTGCATCAGCTGGCGACGAGGTAAGGATGATTAGATAA

AAGGTCCAGTCGTAATGTCCACCGATTCCTTGTAAAGTCGGACCGAT

ACGGCAACCAGTATGTCA
```

wherein, the single underline indicated the universal adapter sequence, the double underline indicated the partition adapter sequence of Partition C, and the framed sequence indicated the index number region.

5. The primers that were complementary to the partition adapters A, B, D, E, F, G, H and the universal adapter sequence were added into the primer library, which was used to perform multiple PCR, so that all 154 sequences in Partitions A, B, D, E, F, G, H were amplified.

Therein, the multiplex PCR adopted touchdown PCR, using Q5® Reaction Buffer Pack kit, and the ratio of two enzymes was Q5:Ex Taq=8:1. The reaction procedure was: 98° C., 5 min; 25 cycles, and the temperature for each cycle was reduced by 0.2° C. (98° C., 20 s; 55.2° C. to 60° C., 30 s; 72° C., 10 s); 72° C., 5 min; 12° C., hold.

6. Through the multiplex PCR amplification and dilution in step 5, an Oligo library containing only Partitions A, B, D, E, F, G and H was obtained.
7. By re-encoding the information of Partition C, new 22 sequences of Partition C were obtained, in which the corrected 58$^{th}$ sequence was as follows (the remaining 21 sequences of Partition C remained unchanged):

```
ATGGTCAGATCGTGCATCACGTATTCACGAAGGGACGAAGACAACTCCT

ATTCATTTTACCAGTTTTGCTTGACGGTTGTCAGAGAGATAACCGAT

ACGGCAACCAGTATGTCA
```

wherein, the single underline indicated the universal adapter sequence, the double underline indicated the partition adapter sequence of Partition C, and the framed sequence indicated the index number region.

At the same time, the content that should be added in line 17 was designed, the original index number region was AGCCTA, two new sequences were added, which index number regions were A-AGCCTA and T-AGCCTA, and the newly added sequences 89-A and 89-B were respectively:

```
Sequence 89-A:
ATGGTCAGATCGTGCATCATGAAATTTGGACCACAGGGCTACAAGTTAT

TACCAGCATAGCTGCCGGACCGGCACACAGATCAAGCCTAAGATCGTG

GACTGCGTAA

Sequence 89-B:
ATGGTCAGATCGTGCATCAGGGTCCTACGATGTGTTGTGCATCATGCTG

AGTGATCTCTAGCCTAAGATCGTGGACTGCGTAA
```

wherein, the single underline indicated the universal adapter sequence, the double underline indicated the partition adapter sequences, and the framed sequence indicated the index number regions.

8. The newly synthesized sequences in step 7 were mixed with the Oligo library obtained in step 6 to obtain a new mixture library.
9. The newly obtained Oligo library in step 8 was subjected to Sanger sequencing.
10. The sequencing result was returned to the computer for decoding, and the correct original file was obtained.
11. The newly obtained Oligo library in step 8 was frozen into dry powder and stored at −20° C.

Example 2: Decoding

The correct Oligo library edited in Example 1 was subjected to sequencing, and the sequence group A after sequencing was subjected to the removal of two ends with length of 18 nt (universal adapter and partition adapter, respectively) to obtain sequence group A'. Firstly, the index number information was read, and the index number was decoded, to obtain numbers of different sizes.

Then, the sequence group A' was rearranged according to the index rule in ascending order, and then the index number was removed to obtain sequence group A".

According to the encoding rules used in Example 1, the nucleic acid sequences of the sequence group A" were transcoded into the corresponding binary codes, the binary codes of all the sequences were connected according to the previous index order, and then the binary codes were read according to the computer language to restore the original file.

What is claimed is:

1. A method for fixed-point editing of a nucleic acid sequence with stored data, which comprises the following steps:

(1) splitting a nucleic acid sequence by which data is stored into a plurality of sequence fragments, and dividing all the sequence fragments into i partitions, wherein i is a positive integer;

(2) adding a theoretical partition adapter at one or both ends of the sequence fragments in each partition, wherein sequence of the partition adapter for each partition is different from each other;

(3) synthesizing the sequence fragments in each partition as described in step (2) to obtain nucleic acid fragments;

(4) determine a partition n where a sequence fragment to be edited is located, and record the partition as the $n^{th}$ partition;

(5) amplifying sequence fragments of all partitions except for sequence fragments of the $n^{th}$ partition by using a partition primer library, wherein the partition primer library comprises primers that are at least partially complementary to sequences of the partition adapter for all partitions except for the $n^{th}$ partition, so as to obtain a library comprising the sequence fragments of all partitions except for the sequence fragments of the $n^{th}$ partition; and (6) correcting a wrong sequence in the sequence fragment to be edited recited in step (4) in the $n^{th}$ partition to obtain a correct sequence, then synthesizing all sequence fragments in the $n^{th}$ partition according to the correct sequence, and adding them into the library of step (5) so as to obtain a library with the correct sequence.

2. The method according to claim 1, characterized by further comprising one or more of the following items:

(a) in step (1), the data is text information, image information, or sound information;

(b) before step (1), the data is encoded into binary data according to a first encoding rule; preferably the first encoding rule is a binary encoding rule; and/or the binary data is encoded into a nucleic acid sequence through a second encoding rule, so as to obtain the nucleic acid sequence by which the data is stored, preferably, the second encoding rule is Huffman Encoding Rule, Fountain Code Encoding Rule, XOR Encoding Rule, or Grass Encoding Rule;

(c) in step (1), the nucleic acid sequence by which a data is stored is split into a plurality of sequence fragments with length of not exceeding 200 nt, in which each fragment has the same length.

3. The method according to claim 1, wherein in step (2), the theoretical partition adapter is added at one or both ends of the sequence fragments in each partition according to any one of the following rules:

a partition adapter A1 is added at one or both ends of each sequence fragment in a 1st partition, a partition adapter A2 is added at one or both ends of each sequence fragment in a 2nd partition, . . . , a partition adapter Ai is added at one or both ends of all sequence fragments in a ith partition, wherein the sequences of the partition adapter are different from each other but have the same length, which is preferably 16-20 nt;

a partition adapter A1 is added at the 5'end of each sequence fragment in a 1st partition, a partition adapter A1' is added at the 3'end of each sequence fragment in the 1st partition, a partition adapter A2 is added at the 5'end of each sequence fragment in a 2nd partition, a partition adapter A2' is added at the 3'end of each sequence fragment in the 2nd partition, . . . , a partition adapter Ai is added at the 5'end of each sequence fragment in a ith partition, and a partition adapter Ai' is added at the 3'end of each sequence fragment in the ith partition, wherein the sequences of the partition adapter are different from each other but have the same length, which is preferably 16-20 nt;

a universal adapter A is added at the 5'end of the sequence fragments of each partition, a partition adapter A1 is added at the 3'end of each sequence fragment in a 1st partition, a partition adapter A2 is added at the 3'end of each sequence fragment in a 2nd partition, . . . , a partition adapter Ai is added at the 3'end of each sequence fragment in a ith partition, wherein the sequences of the partition adapter are different from each other but have the same length, which is preferably 16-20 nt; or a universal adapter A is added at the 3'end of the sequence fragments in each partition, a partition adapter A1 is added at the 5'end of each sequence fragment in a 1st partition, a partition adapter A2 is added at the 5'end of each sequence fragment in a 2nd partition, . . . , a partition adapter Ai is added at the 5'end of each sequence fragment in a ith partition, wherein the sequences of the partition adapter are different from each other but have the same length, which is preferably 16-20 nt.

4. The method according to claim 1, wherein the sequence fragments in the library in step (6) are stored in a medium, or the sequence fragments in the library in step (6) are connected to a vector, and the vector is stored in a medium, or the sequence fragments in the library in step (6) are assembled, and the assembled sequence fragments are stored in a medium, preferably, the medium is selected from liquid phase, dry powder, living cells, or a combination thereof.

5. The method according to claim 1, wherein after a sequence fragment added with a theoretical partition adapter is obtained in step (2), the sequence fragment is added with an index number, wherein the index number is adjacent to the theoretical partition adapter.

6. The method according to claim 5, wherein the partition adapter has a length of 18 nt, and the index number sequence has a length of 5 nt to 10 nt, preferably 6 nt.

7. The method according to claim 1, wherein the partition n where the sequence fragment to be edited is located is determined by the following method:

the partition n where the sequence fragment to be edited is located is determined according to encoding rules used when data is stored, or the partition n where the sequence fragment to be edited is located is determined by sequencing the nucleic acid sequence fragment synthesized in step (3) and performing sequence alignment.

8. The method according to claim 1, wherein in step (5), a multiplex PCR is used to amplify the sequence fragments, preferably, the multiplex PCR is Touch up, or Touch down PCR, preferably, the polymerase used is selected from Taq, Phusion, Q5, Vent, KlenTaq, or a combination thereof.

9. A decoding method, comprising sequencing the library obtained by using the method according to claim 1 to obtain sequences of each sequence fragment; and obtaining the order of each sequence fragment according to index number of the each sequence fragment; splicing the sequences of each sequence fragments according to the order to obtain the nucleic acid sequence by which the data is stored;

optionally, the obtained nucleic acid sequence by which the data is stored is transcoded into a corresponding binary code, and then the binary code is transcoded into a corresponding data information.

* * * * *

SEQUENCE LISTING

```
<160> NUMBER OF SEQ ID NOS: 4

<210> SEQ ID NO 1
<211> LENGTH: 114
<212> TYPE: DNA
<213> ORGANISM: artificial sequence
<220> FEATURE:
<223> OTHER INFORMATION: the mismatched 58th sequence

<400> SEQUENCE: 1
```

-continued

```
atggtcagat cgtgcatcag ctggcgacga ggtaaggatg attagataaa aggtccagtc     60

gtaatgtcca ccgattcctt gtaaagtcgg accgatacgg caaccagtat gtca          114


<210> SEQ ID NO 2
<211> LENGTH: 114
<212> TYPE: DNA
<213> ORGANISM: artificial sequence
<220> FEATURE:
<223> OTHER INFORMATION: the corrected 58th sequence

<400> SEQUENCE: 2

atggtcagat cgtgcatcac gtattcacga agggacgaag acaactccta ttcattttac     60

cagttttgct tgacggttgt cagagagata accgatacgg caaccagtat gtca          114


<210> SEQ ID NO 3
<211> LENGTH: 107
<212> TYPE: DNA
<213> ORGANISM: artificial sequence
<220> FEATURE:
<223> OTHER INFORMATION: the added sequence 89-A

<400> SEQUENCE: 3

atggtcagat cgtgcatcat gaaatttgga ccacagggct acaagttatt accagcatag     60

ctgccggacc ggcacacaga tcaagcctaa gatcgtggac tgcgtaa                  107


<210> SEQ ID NO 4
<211> LENGTH: 83
<212> TYPE: DNA
<213> ORGANISM: artificial sequence
<220> FEATURE:
<223> OTHER INFORMATION: the added sequence 89-B

<400> SEQUENCE: 4

atggtcagat cgtgcatcag ggtcctacga tgtgttgtgc atcatgctga gtgatctcta     60

gcctaagatc gtggactgcg taa                                             83
```